US00PP35781P2

(12) United States Plant Patent
Olesen

(10) Patent No.: US PP35,781 P2
(45) Date of Patent: Apr. 30, 2024

(54) FLORIBUNDA ROSE PLANT NAMED 'POULCAS073'

(50) Latin Name: *Rosa hybrida*
Varietal Denomination: Poulcas073

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,478

(22) Filed: Sep. 8, 2023

(30) Foreign Application Priority Data

Sep. 30, 2022 (QZ) ..... PBR 2022/2151

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./101, 141, 148
See application file for complete search history.

*Primary Examiner* — Susan McCormick Ewoldt

(57) ABSTRACT

A new garden rose plant of the Compact Floribunda class which has abundant, pink flowers and attractive foliage. This new and distinct variety has shown to be uniform and stable in the resulting generations from asexual propagation.

3 Drawing Sheets

Botanical designation: *Rosa hybrida.*

Variety denomination: 'Poulcas073'.

This application claims priority to Plant Breeder's Rights Application Number 2022/2151, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulcas073', originated as a single seedling from the stated cross.

The new variety may be distinguished from its male pollen parent and female seed parent primarily by the following characteristics. The male pollen parent plant has apricot coloured flowers and grows to a height of 40 cm while the new variety has pink flowers and grows to a height of 60 cm. The female seed parent plant has a growth height of 85 to 100 cm while the newly claimed plant grows to 60 cm. The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulcas073' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulcas073' was selected in the spring of 2015 by the inventor as a single plant from the progeny of the aforementioned hybridization.

Asexual reproduction of 'Poulcas073' by rooted cuttings was first done by Mogens N. Olesen in the nursery in Fredensborg, Denmark in July, 2015. This initial and other subsequent asexual propagations conducted in controlled environments have demonstrated that the characteristics of 'Poulcas073' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas073'.

Specifically illustrated in FIG. 1 of the drawings are open flowers viewed from above and the side, flower buds at various stages of development, sepals detached revealing the receptacle and flower parts, and flower petals detached.

Figure 1:
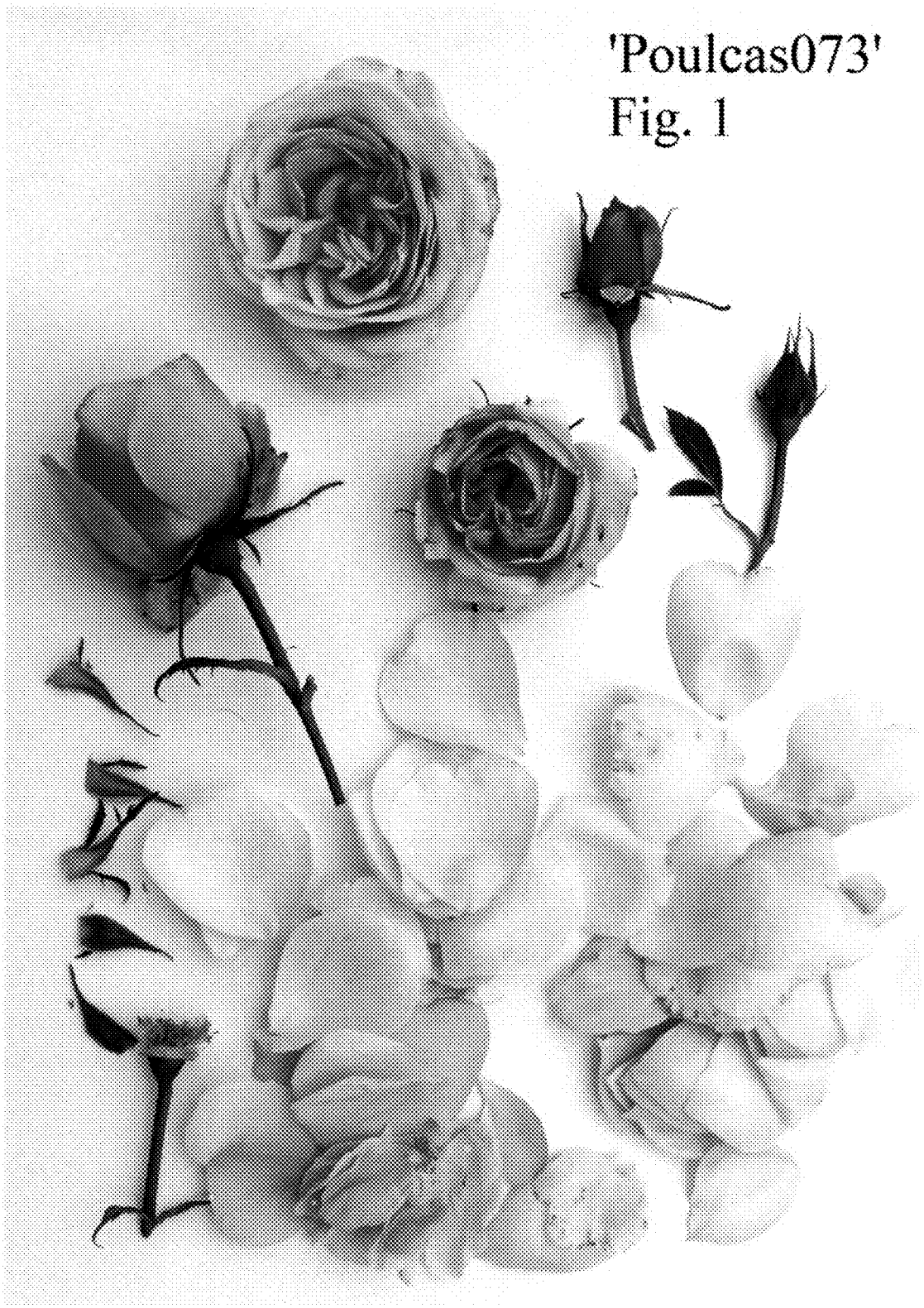
Figure 2:
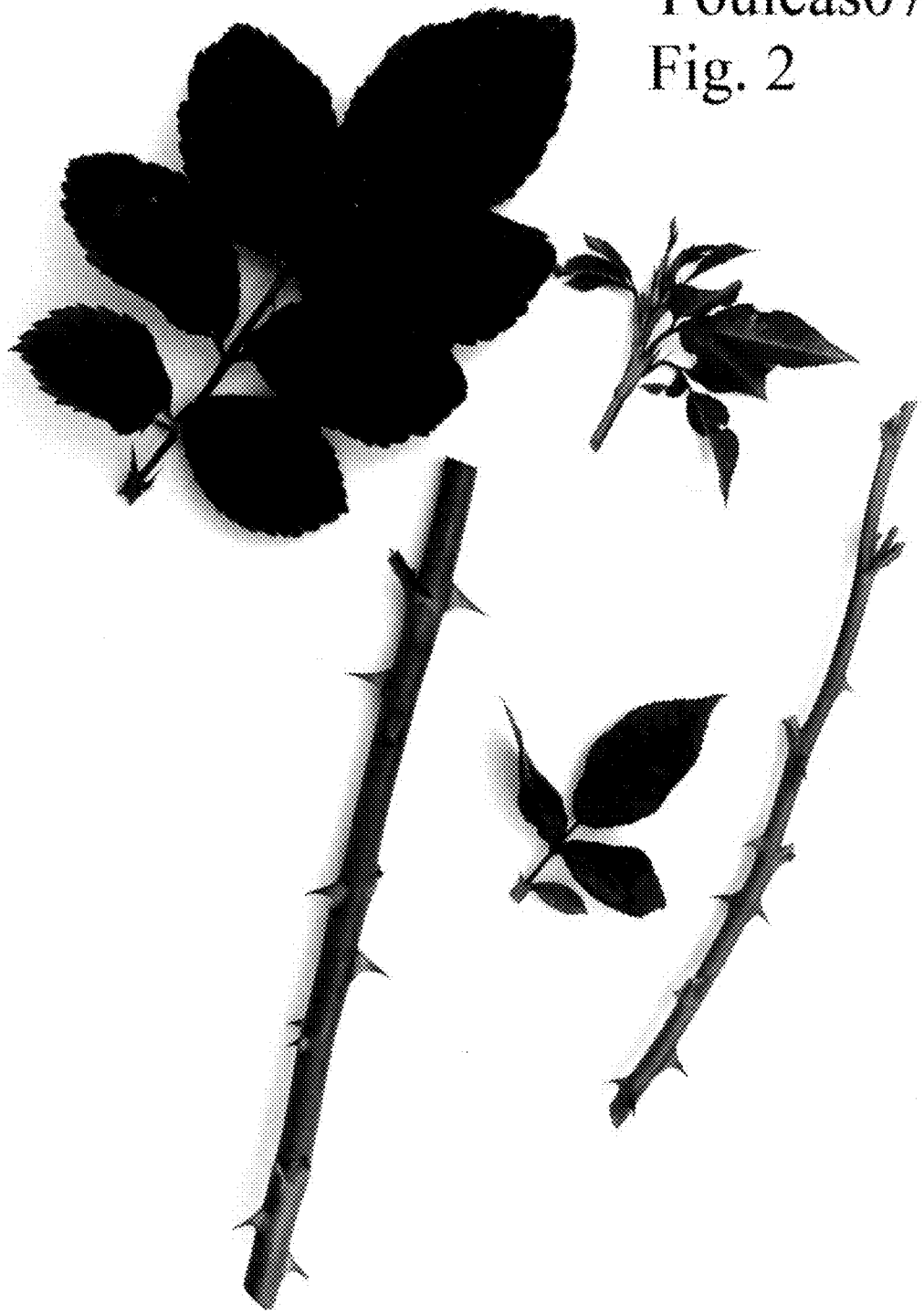

Specifically illustrated in FIG. 2 of the drawings are mature and juvenile leaves, mature and juvenile stems showing prickles.

Figure 3:
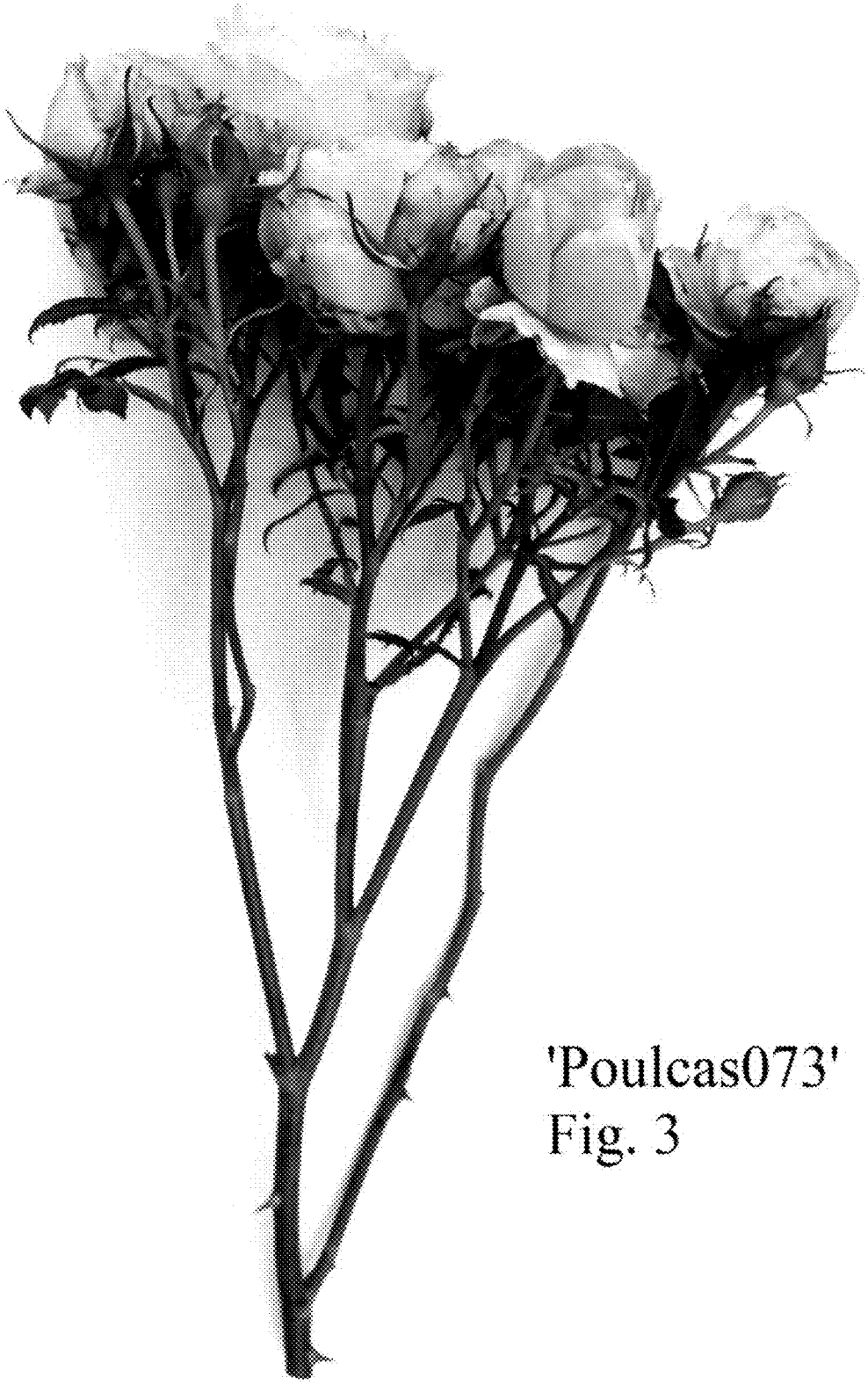

FIG. 3 shows a cluster of open flowers on a branch. Plants shown are 1.5 years of age.

DETAILED DESCRIPTION OF THE VARIETY

The following is a description of 'Poulcas073', as observed in its growth in an outdoor nursery in Odense Denmark. Observed plants are 18 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulcs009', U.S. Plant Pat. No. 15,875 are compared to the claimed plant. While 'Poulcas073' has 60 flower petals, 'Poulcs009' has 50 flower petals. The claimed plant has a flower diameter of 70 mm while 'Poulcs009' has a flower diameter of 50 mm. Open flowers of 'Poulcas073' are generally Red-Purple 62B and Red Group 52C in color while 'Poulcs009' has a general tonality of Red Group 52B.

FLOWER AND FLOWER BUD

Blooming habit: Continuous.

Flower bud:

- *Size*.—Upon opening, 24 mm in length from base of receptacle to end of bud. Bud diameter is 13 mm.
- *Bud form*.—Ovoid.
- *Bud color*.—As sepals divide petals are Orange-Red Group 35A and Red Group 46B.
- *Sepal inner surface*.—Color: Yellow-Green Group 144A. Surface: Lightly pubescent.
- *Sepal outer surface*.—Color: Yellow-Green Group 144A with intonations of Greyed-Red Group 180C. Texture: Smooth.
- *Sepal shape*.—Apex: Cirrhose. Base: Flat at union with receptacle.
- *Sepal margin*.—Margins have moderate to strong foliaceous appendages on three of the five sepals.
- *Sepal size*.—34 mm long, 9 mm wide.
- *Receptacle*.—Texture: Smooth. Size: 9 mm in height, 9 mm wide. Color: Yellow-Green Group 144A with intonations of Greyed-Red Group 180A. Shape: Both campanulate and funnel.
- *Pedicel*.—Surface: Smooth. Length: About 30 mm. Diameter: 3 mm on average. Color: Yellow-Green Group 144A with intonations of Greyed-Red Group 179B. Strength: Strong.
- *Peduncle*.—Length: 30 to 140 mm. Diameter: 3 to 4 mm. Color: Yellow-Green Group 144A. Texture: Smooth.

Flower bud development: Flower buds are borne in clusters of about 7 to 15 flower buds per stem. Development as a compound corymb.

Flower bloom:

- *Fragrance*.—Moderate honey like rose scent.
- *Duration*.—The blooms have a duration on the plant of approximately 20 days. Petals fall cleanly away from plant after flowers have fully matured.
- *Size*.—Flower diameter is 70 mm when open. Flower depth is 40 mm.
- *Flower shape*.—Cupped, globose, quartered-rosette with many overlapping petals packed into quarter sections.
- *Shape of flower, side view*.—The upper portion is flat. The lower portion is flat concave.

Petalage: Under normal conditions, flowers have about 60 petals.

General tonality of flower: Open flowers are Red-Purple 62B and Red Group 52C. After 10 days Red-Purple Group 62C.

Petal color:

- *Upon opening, outer petals*.—Upper surface: Marginal zone is Red-Purple Group 62C. Middle zone Orange Group 29C. Basal zone Yellow Group 4A. Lower surface: Red-Purple Group 62B with other intonations of Red-Purple Group 62D. Basal zone Yellow Group 4A.
- *Upon opening, inner petals*.—Upper surface: Orange-Red Group 31C at the marginal zone, blended with Orange Group 24C at the middle and basal zone. Petal spot Yellow Group 5B. Lower surface: Marginal zone Red-Purple Group 62C. Middle and basal zone Red Group 37B. No petal spot.
- *After opening, outer and inner petals*.—Upper surface: Marginal zone White Group N155B. The middle zone is Red-Purple Group 62B. Green White 157A at the basal zone. Lower surface: Marginal zone White Group N155B. The middle zone is Red-Purple Group 62B. Green White 157A at the basal zone. Spots of Red-Purple Group 61B.

Petals:

- *Petal reflex*.—Very lightly reflexed.
- *Margin*.—Uniform and entire. Many petals also have a single cleft at the apex. Light undulations.
- *Shape*.—Broad and elliptic. Apex shape: Rounded. Base shape: Acute.
- *Size*.—47 mm (l)×48 mm (w).
- *Texture*.—Smooth.
- *Thickness*.—Average.

Petaloids:

- *Size*.—20 mm (l) by 13 mm (w).
- *Quantity*.—About 12.
- *Shape*.—Elliptical with an acute base and rounded apex.
- *Color*.—Red-Purple Group 62C on the upper and lower surface.

Reproductive flower parts:

- *Pollen*.—None observed.
- *Anthers*.—Size: 2 mm in length. Color: Yellow Group 3C. Quantity: 45 on average.
- *Filaments*.—Color: Green Yellow 1C. Length: 5 mm.
- *Pistils*.—Length: 4 mm. Quantity: 35 on average.
- *Stigmas*.—Color: Yellow-White Group 158A.
- *Styles*.—Color: Red Group 53B.
- *Location of stigmas*.—Level in location relative to the length of the filaments and the height of the anthers.
- *Hips*.—None Observed.

PLANT CHARACTERISTICS

Plant growth: Upright and bushy. Plants are 60 cm in height, and 70 cm wide.

Stems:

- *Color of juvenile growth*.—Yellow-Green Group 144A.
- *Color of mature growth*.—Yellow-Green Group 144A.
- *Length*.—Canes are about 35 cm from the base of the plant to the flowering portion.
- *Diameter*.—About 7 to 8 mm.
- *Internodes*.—On mature canes about 65 mm between nodes.
- *Surface texture*.—Young wood: Smooth. Older wood: Smooth.

Long prickles:

- *Incidence*.—About 7 prickles per 10 cm of stem.
- *Size*.—Average length of prickles on mature stems is 11 mm.
- *Shape*.—Upper portion is linear. Lower portion is concave.

*Color*.—Juvenile prickles: Yellow-Green Group 146C with intonations of Greyed-Purple Group 183B. Mature prickles: Greyed-Yellow Group 161A with intonations of Greyed-Purple Group 185A.

Plant foliage:

*Compound leaf*.—160 mm (l)×100 mm (w).

*Quantity*.—2 leaves per 10 cm of stem on average.

*Leaf bearing angle to the stem*.—90 degrees.

*Color of juvenile foliage*.—Upper side: Yellow-Green Group 146A with shaded intonations of Greyed-Purple Group 187A. Lower side: Yellow-Green Group 144B with intonations of Greyed-Purple Group 187C.

*Color of mature foliage*.—Upper side: Yellow-Green Group 147A. Lower side: Yellow-Green Group 147B.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 146A.

*Petiole*.—Length: 20 mm. Diameter: 2 mm. Upper surface color: Yellow-Green Group 144A. Lower surface color: Yellow-Green Group 144A.

*Rachis*.—Length: 62 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 71 mm long, 44 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcas073' substantially as described and illustrated herein.

* * * * *

'Poulcas073'

'Poulcas073'

'Poulcas073'